United States Patent
Mohler et al.

(10) Patent No.: US 8,241,845 B2
(45) Date of Patent: Aug. 14, 2012

(54) STEROID 5α-REDUCTASE

(75) Inventors: James L. Mohler, Buffalo, NY (US);
Mark Titus, Chapel Hill, NC (US);
Olga Kozyreva, Chapel Hill, NC (US);
O. Harris Ford, III, Wake Forest, NC (US); Elsbieta Kawinski, Orchard Park, NY (US); Yun Li, Orchard Park, NY (US)

(73) Assignee: Health Research Inc., Buffalo, NY (US)

( * ) Notice: Subject to any disclaimer, the term of this patent is extended or adjusted under 35 U.S.C. 154(b) by 185 days.

(21) Appl. No.: 12/404,590

(22) Filed: Mar. 16, 2009

(65) Prior Publication Data

US 2009/0246785 A1   Oct. 1, 2009

Related U.S. Application Data

(62) Division of application No. 11/432,424, filed on May 10, 2006, now abandoned.

(60) Provisional application No. 60/679,497, filed on May 10, 2005.

(51) Int. Cl.
*C12Q 1/68*   (2006.01)
*C12Q 1/26*   (2006.01)
*C12N 15/53*  (2006.01)
*C12N 9/02*   (2006.01)

(52) U.S. Cl. .............................. 435/6; 435/25; 435/189

(58) Field of Classification Search .................. None
See application file for complete search history.

(56) References Cited

U.S. PATENT DOCUMENTS

2002/0086387 A1   7/2002   Meyers et al.

FOREIGN PATENT DOCUMENTS

| WO | WO 0020604 | 4/2000 |
| WO | WO 0179504 | 10/2001 |

OTHER PUBLICATIONS

Sweat, et al.; Preparation and Characterization of the Enzyme Which Converts Testosterone to Androstenedione; The Journal of Biological Chemistry; 185(1), 1950; pp. 75-84.

*Primary Examiner* — Rebecca E. Prouty
(74) *Attorney, Agent, or Firm* — Hodgson Russ LLP (57) ABSTRACT

The invention provides an isolated, novel steroid 5α-reductase enzyme termed SRD5AIII. The protein has an estimated molecular weight of 37 kDa and is capable of converting testosterone to dihydrotestosterone at a pH of about 7.0. Also provided is a method for identifying inhibitors of SRD5AIII by contacting SRD5AIII with a test compound and measuring the activity of the enzyme. A reduced activity relative to a control indicates that the test compound is an inhibitor of SRD5AIII. A method is also provided for detecting androgen stimulated prostate cancer or recurrent prostate cancer in an individual. The method comprises obtaining a prostate biopsy from an individual and determining the level of expression of SRD5AIII gene or protein relative to a normal control. An increased expression of SRD5AIII relative to the control is indicative of androgen stimulated prostate cancer or recurrent prostate cancer.

5 Claims, 6 Drawing Sheets

Figure 1A AS-BP
Figure 1B AS-CaP
Figure 1C Recurrent CaP

STEROID 5α-REDUCTASE

This application is a divisional of and claims priority to U.S. patent application Ser. No. 11/432,424, filed on May 10, 2006, now abandoned, which in turn claims priority to U.S. provisional application Ser. No. 60/679,497, filed May 10, 2005, the entire disclosures of each of which are incorporated herein by reference.

FIELD OF THE INVENTION

This invention relates generally to steroid 5α-reductase enzymes and more particularly to a novel isozyme of steroid 5α-reductase.

DESCRIPTION OF RELATED ART

Androgen target cells in peripheral tissues use testosterone to activate androgen receptor, which interacts with androgen response elements in DNA to regulate gene transcription. Alternatively, intracellular testosterone (T) acts as a prohormone that is converted to dihydrotestosterone (DHT), a more potent androgen receptor ligand. In the prostate, an intracrine pathway (Labrie F. Intracrinology. Mol Cell Endocrinol 1991; 78(3):C113-118) utilizes the enzyme steroid 5α-reductase (SRD5A; EC 1.3.99.5) to metabolize testosterone to DHT. The adrenal androgen androstenedione (ASD) is also converted to 5α-reduced androstanedione by SRD5A in the prostate (Hsing et al. Prostate 2002; 52(3):213-235) and ASD has been implicated as a source of DHT in prostate tissue after castration (Belanger et al. J Steroid Biochem 1989; 32(5): 695-698).

SRD5A isozymes I (SRD5AI) and II (SRD5AII) are membrane-associated, NADPH-dependent enzyme that catalyze the irreversible stereo-specific reduction of $C^{19}$ 3-keto-$\Delta^{4-5}$ steroid to 5α-reduced metabolites. SRD5A I and II in humans are composed of 260 and 254 amino acids, respectively, with molecular weights of 29.4 kDa and 28.4 kDa, respectively, and with 47% sequence identity and distinct biochemical properties (Russell et al. Annu Rev Biochem 1994; 63:25-61). SRD5AI exhibits a broad neutral to basic optimum pH range, while SRD5AII displays a narrow acid pH optimum for maximum activity. Both isozymes contain an N-terminal steroid binding domain and a C-terminal NADPH binding domain. SRD5AI has higher turnover and decreased substrate affinity whereas SRD5AII has lower turnover and increased substrate affinity. The apparent dissociation constant for NADPH cofactor is similar for both isozymes.

The enzyme SRD5A has been implicated in endocrine abnormalities including prostate hyperplasia. Prostate cancer (CaP) is the second leading cause of death and the most common non-skin cancer in American men. Current estimates predict 234,460 new cases of CaP in American men and 27,350 deaths from CaP in 2006 (Jemal et al. 2006. CA Cancer J Clin 2006; 56(1):106-30). Men who fail curative therapy or present with advanced disease usually receive androgen deprivation therapy that causes regression of androgen-dependent CaP through programmed cell death (Denmeade et al. Prostate 1996; 28(4):251-265). However, androgen deprivation therapy is palliative (Huggins et al. Arch Surg 1941; 43:209-212) since CaP recurs and almost always causes death. A molecular role for androgen receptor in the transition from androgen-stimulated CaP to recurrent CaP is supported by androgen receptor expression in recurrent CaP (de Vere White et al. Eur Urol 1997; 31(1):1-6; Culig et al. Prostate 1998; 35(1):63-70; Mohler et al. Clin Cancer Res 2004; 10(2):440-448) and expression of androgen-regulated genes (Mohler et al. Clin Cancer Res 2004; 10(2):440-448; Gregory et al. Cancer Res 1998; 58(24):5718-5724; Mousses et al. Oncogene 2001; 20(46):6718-6723). Potential mechanisms include androgen receptor amplification (Visakorpi et al. Nat Genet. 1995; 9(4):401-406), androgen receptor gene mutations leading to transactivation by low levels of DHT (Culig et al. Microsc Res Tech 2000; 51(5):447-455) or promiscuous ligand binding (Tan et al. Mol Endocrinol 1997; 11(4):450-459) and posttranslational modification of androgen receptor through peptide growth factor signaling (Feldman et al. Nat Rev Cancer 2001; 1 (1):34-45; Arnold et al. Endocr Relat Cancer 2002; 9(1):61-73). In addition to these mechanisms, recent investigations have found tissue levels of T and DHT in recurrent CaP that are sufficient for activation of even wild-type androgen receptor (Mohler et al. Clin Cancer Res 2004; 10(2):440-448).

Currently available SRD5A inhibitors include finasteride, which is selective for SRD5AII and two bispecific SRD5A inhibitors, LY320236 (Lily) and Dutasteride (GlaxoSmithKline). However, neither finasteride nor dutasteride inhibits SRD5A activity completely. Lack of efficacy of finasteride, a S5αRII specific inhibitor, as treatment for CaP suggests that SRD5AII does not contribute significantly to DHT production (Thompson et al. N Engl J Med 2003; 349(3):215-224). Further, blockade of SRD5AI and SRD5AII by LY305736 in nine men with recurrent CaP produced serum prostate-specific antigen (PSA) reduction without complete remission (Eisenberger et al. Urology 2004; 63(1):114-119). Early results from use of the bispecific SRD5A inhibitor, dutasteride, administered to patients at Roswell Park Cancer Institute, suggest incomplete remission. Therefore, it is clear that there continues to be a need in the field of prostate cancer to identify new therapeutic approaches for inhibiting SRD5A. The present invention provides tools for addressing this need.

SUMMARY OF THE INVENTION

The present invention provides an isolated steroid 5α-reductase enzyme. The enzyme is termed "SRD5AIII." The SRD5AIII protein has an estimated molecular weight of approximately 37 kDa as measured from SDS PAGE analysis. SRD5AIII is demonstrated to be capable of converting testosterone (T) to dihydrotestosterone (DHT) at a pH of 7.0. The amino acid sequence of SRD5AIII is provided as SEQ ID NO:2. A polynucleotide encoding SRD5AIII is provided as SEQ ID NO:1. The present invention also provides an expression vector comprising a polynucleotide encoding SRD5AIII. In one embodiment, the sequence encoding SRD5AIII comprises the sequence of SEQ ID NO:1 from nucleotide 93 to nucleotide 1049.

Also provided is a method for identifying inhibitors of SRD5AIII. The method comprises contacting SRD5AIII with a test compound and T, measuring the activity of the enzyme, and comparing the activity to a control, i.e., in the absence of the test compound. A reduced activity relative to the control is indicative that the test compound is an inhibitor of SRD5AIII. In particular embodiments, the enzyme activity is measured as the rate of conversion of T to DHT or androstanedione.

Also provided is a method for detecting androgen stimulated prostate cancer or recurrent prostate cancer in an individual. The method comprises the steps of obtaining a biopsy from the prostate of the individual and determining the level of expression of SRD5AIII gene or protein. The expression level is compared to that from a normal control. An increased expression of SRD5AIII relative to the control is indicative of androgen stimulated prostate cancer or recurrent prostate cancer. SRD5AIII expression levels can be determined by measuring mRNA or protein levels.

DETAILED DESCRIPTION OF THE INVENTION

In the present invention a novel SRD5A isozyme has been identified. This isozyme is termed "SRD5AIII." The isozyme is encoded by a cDNA, the sequence of which was published as one of 21,243 cDNAs sequenced as part of the "full-length long Japan" (FLJ) cDNA collection (Ota et al. Nat Genet. 2004; 36(1):40-45). The nucleotide sequence of the cDNA and its deduced amino acid sequence are recorded in GenBank as accession no. BC002480. The GenBank entry indicates that the sequence is "5 alpha-reductase 2-like". However, the protein sequence of SRD5AIII has only 25% homology with SRD5AII and 20% homology with SRD5AI. Previous attempts by other researchers to express this protein recombinantly have failed (personal communications) and it has therefore not been possible to analyze its expression or enzymatic activity.

We obtained the SRD5AIII cDNA from Dr. Juergen Reichert of the University of Southern California Medical Center and have now successfully expressed it recombinantly. We have now also demonstrated that SRD5AIII has androgen 5α-reducing activity, and that it is expressed at similar levels in recurrent CaP and AS-CaP, but maintained at higher levels than either SRD5AI or SRD5AII in recurrent CaP. We have also demonstrated that tissue levels of T are similar in androgen-stimulated benign prostate and recurrent CaP. However, T is 5α-reduced to DHT in benign prostate so that T levels are lower than DHT levels. Tissue levels of DHT in recurrent CaP are reduced by 90% but remain 1.45 nanomolar, a level sufficient for activation for even wild type androgen receptor. (DHT tissue levels were confirmed using liquid chromatography tandem mass spectrometry (LC/MS/MS). Recurrent CaP median tissue DHT levels measured in 18 specimens by LC/MS/MS were 1.25 nanomolar.) Therefore, and without intending to be bound by any particular theory, it is believed that SRD5AIII may play a role in a new paradigm: CaP that recurs after medical or surgical castration is not "androgen-independent" but uses tissue levels of DHT to activate the androgen receptor and express androgen-regulated genes necessary for growth. Recurrent CaP appears to have developed the ability to synthesize tissue levels of T and DHT sufficient for androgen receptor activation in spite of the absence of circulating levels of testicular androgens. Thus, recognition of the presence of tissue DHT in recurrent CaP provides a new target for novel therapies.

Accordingly, in one embodiment, this invention provides expression vectors comprising polynucleotides which encode SRD5AIII. Any nucleic acid sequence which encodes the amino acid sequence of SRD5AIII can be used in the expression vector to generate recombinant molecules which express SRD5AIII. In a particular embodiment, the invention provides expression vectors which comprise a polynucleotide which is 1094 bases in length. The coding sequence is from nucleotide 93 to 1049 of SEQ ID NO:1. The poly A tail (33 bases) does not align to the human genome. The sequence of a polynucleotide encoding SRD5AIII is shown below as SEQ ID NO:1.

```
                                       (SEQ ID NO: 1)
ctgagaccgg tgcgccgcgc gctagtggcc gctcttccgc gggctagcgg gcggtggggg cgccagcagc gcggaaggcg ggcacgcggg ccatggctcc ctgggcggag gccgagcact cggcgctgaa cccgctgcgc gcggtgtggc tcacgctgac cgccgccttc ctgctgaccc tactgctgca gctcctgccg cccggcctgc tcccgggctg cgcgatcttc caggacctga tccgctatgg gaaaaccaag tgtggggagc cgtcgcgccc cgccgcctgc cgagcctttg atgtcccccaa gagatatttt tcccactttt atatcatctc agtgctgtgg aatggcttcc tgctttggtg ccttactcaa tctctgttcc tgggagcacc
```

-continued

```
ttttccaagc tggcttcatg gtttgctcag aattctcggg gcggcacagt tccagggagg ggagctggca ctgtctgcat tcttagtgct agtatttctg tggctgcaca gcttacgaag actcttcgag tgcctctacg tcagtgtctt ctccaatgtc atgattcacg tcgtgcagta ctgttttgga cttgtctatt atgtccttgt tggcctaact gtgctgagcc aagtgccaat ggatggcagg aatgcctaca taacagggaa aaatctattg atgcaagcac ggtggttcca tattcttggg atgatgatgt tcatctggtc atctgcccat cagtataagt gccatgttat tctcggcaat ctcaggaaaa ataaagcagg agtggtcatt cactgtaacc acaggatccc atttggagac tggtttgaat atgtttcttc ccctaactac ttagcagagc tgatgatcta cgtttccatg gccgtcacct ttgggttcca caacttaact tggtggctag tggtgacaaa tgtcttcttt aatcaggccc tgtctgcctt tctcagccac caattctaca aaagcaaatt tgtctcttac ccgaagcata ggaaagcttt cctaccattt ttgttttaag ttaacctcag tcatgaagaa tgcaaaccag gtgatggttt caatgcctaa ggacagtgaa gtctggagcc caaagtacag tttcagcaaa gctgtttgaa actctccatt ccatttctat accccacaag ttttcactga atgagcatgg cagtgccact caagaaaatg aatctccaaa gtatcttcaa agaataaata ctaatggcag aaaaaaaaaa aaaaaaaaaa aaaaaaaaaa aaaa.
```

It will be appreciated by those skilled in the art that as a result of the degeneracy of the genetic code, a multitude of nucleotide sequences encoding SRD5AIII may be produced. Further, various single nucleotide polymorphisms (SNPs) may be associated with SRD5AIII genes. Thus, the invention contemplates expression vectors comprising all possible variation of nucleotide sequence that could be made by selecting combinations based on possible codon choices. These combinations are made in accordance with the standard triplet genetic code as applied to the nucleotide sequence of naturally occurring SRD5AIII.

This invention also provides purified steroid 5α-reductase III. The polypeptide is 318 amino acids long. The sequence is provided in SEQ ID NO:2 and shown below. Its deduced molecular weight is 36.5 kDa.

(SEQ ID NO: 2)
MAPWAEAEHSALNPLRAVWLTLTAAFLLTLLLQLLPPGLLPGCAIFQDLI

RYGKTKCGEPSRPAACRAFDVPKRYFSHFYIISVLWNGFLLWCLTQSLFL

GAPFPSWLHGLLRILGAAQFQGGELALSAFLVLVFLWLHSLRRLFECLYV

SVFSNVMIHVVQYCFGLVYYVLVGLTVLSQVPMDGRNAYITGKNLLMQAR

WFHILGMMMFIWSSAHQYKCHVILGNLRKNKAGVVIHCNHRIPFGDWFEY

VSSPNYLAELMIYVSMAVTFGFHNLTWWLVVTNVFFNQALSAFLSHQFYK

SKFVSYPKHRKAFLPFLF

The homology between the three isozymes is as follows: SRD5AI versus SRD5AII 47% sequence identity; SRD5AI versus SRD5AIII 20% sequence identity; SRD5AII versus SRD5AIII 25% sequence identity. The recombinant or purified enzyme can be used for drug discovery using standard, artificial in vitro assays. Bioassays using well-characterized CaP cell lines and CaP xenografts can be used to confirm assay results in vitro and in vivo. Finally, frozen specimens of androgen-stimulated benign prostate, androgen-stimulated CaP and recurrent CaP can be used for final preclinical testing.

In one aspect, the invention provides purified SRD5AIII polypeptides. Such peptides are capable of converting T to DHT, and comprise an amino acid sequence that has greater than about 70% amino acid sequence identity, preferably about 75, 80, 85, 90, or 95% amino acid sequence identity, to SEQ ID NO: 2. Determination of sequence identity between two polypeptides is well within the purview of those skilled in the art. In a preferred embodiment, the polypeptides of the present invention comprise an amino acid sequence which is 98 or 99% identical to SEQ ID NO: 2.

The purified polypeptides of the present invention also include sequences having conservative substitutions which are based generally on relative similarity of R-group substituents. As examples, these substitutions include gly or ser for als; lys for arg; gln or his for asn; glu for asp; ser for cys; asn for gln; asp for glu; ala for gly; asn or gln for his; leu or val for ile; ile or val for leu; arg for lys; leu or tyr for met; thr for ser; tyr for trp; phe for tyr; and ile or leu for val.

Also provided are methods of expressing or isolating the polypeptides of the invention. In one embodiment, the polypeptide can be isolated from cells or tissue sources that express the protein naturally by an appropriate purification scheme using standard protein purification techniques. In another embodiment, polypeptides of the invention are produced by recombinant DNA techniques. Alternatively, a polypeptide of the invention can be synthesized in an in vitro translation system. Further, a polypeptide of the invention can be synthesized chemically using standard peptide synthesis techniques.

Polypeptides of the invention can be recombinantly expressed by cloning DNA molecules of the invention into an appropriate expression vector, introducing such a vector into prokaryotic or eukaryotic host cells, and growing the host cells under conditions suitable for production of recombinant SRD5AIII protein. The expression vector-containing cells can be clonally propagated and analyzed to determine the production of SRD5AIII protein. Identification of host cell clones that express S5ARIII can be done using routine techniques such as immunological reactivity with antibodies toSRD5AIII. Affinity columns containing such antibodies can be used to purify the recombinant polypeptides. Recombinant methodologies are described in detail in Maniatis et al. (2004).

Polypeptides of the invention can also be produced using an in vitro translation and/or transcription system. Such methods are known to those skilled in the art. For example, SRD5AIII mRNA can be translated in various cell-free systems, including, but not limited to, wheat germ extracts and reticulocyte extracts. Alternatively, the coding sequence of SRD5AIII cDNA can be cloned under the control of a suitable promoter (such as T7 promoter). Then, using this construct as the template, SRD5AIII protein can be produced in an in vitro transcription and translation system, for example using a Reticulocyte Lysate System such as that commercially available.

Polypeptides of the invention can also be produced by chemical synthesis, such as solid phase peptide synthesis on an automated peptide synthesizer, using known amino acid sequences or amino acid sequences derived from the DNA sequence of the genes of interest. Such methods are known to those skilled in the art.

The present invention also provides antibodies to SRD5AIII. The antibodies may be polyclonal, monoclonal, or antibody fragments e.g., single chain Fv, Fab', F(ab')$_2$ etc., that specifically bind SRD5AIII.

Polyclonal antibodies directed to SRD5AIII protein can be prepared by immunizing a suitable subject with the protein. For the production of antibodies, various hosts including goats, rabbits, rats, mice, humans, and others, may be immunized by injection with SRD5AIII or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable The antibody titer in the immunized subject can be monitored over time using standard techniques, such as with an enzyme linked immunosorbent assay (ELISA) using immobilized proteins. If desired, the antibody molecules directed against SRD5AIII protein can be isolated from the mammal (e.g., from the blood) and further purified by well known techniques, such as protein A chromatography, to obtain the IgG fraction.

Monoclonal antibodies directed toward SRD5AIII protein can also be produced by standard techniques. Briefly, an immortal cell line (typically a myeloma) is fused to lymphocytes (typically splenocytes) from a mammal immunized with a SRD5AIII protein or antigenic fragments thereof, and the culture supernatants of the resulting hybridoma cells are screened to identify a hybridoma producing a monoclonal antibody that binds SRD5AIII protein. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Hybridoma cells resulting from the fusion producing a monoclonal antibody of the invention are detected by screening the hybridoma culture supernatants for antibodies that bind SRD5AIII protein, e.g., using a standard ELISA assay. Human hybridomas can be prepared in a similar way. Other techniques such as the human B-cell hybridoma technique, and the EBV-hybridoma technique can also be used. These techniques are known in the art; (see, i.e., Kohler et al. Nature 1975; 256(5517):495-497; Kozbor et al. J Immunol Methods 1985; 81(1):31-42; Cote et al. Proc Natl Acad Sci USA 1983; 80(7):2026-2030; Cole et al. Mol Cell Biochem 1984; 62(2): 109-120).

An alternative to preparing monoclonal antibody-secreting hybridomas is to identify and isolate monoclonal antibodies by screening a recombinant combinatorial immunoglobulin library (e.g., an antibody phage display library) with SRD5AIII protein.

If peptide fragments of SRD5AIII are used for the production of antibodies, the peptide fragments preferably are at least five amino acids long, and more preferably at least 10 amino acids long. It is also preferable that they are identical to a portion of the amino acid sequence of the natural protein. Short stretches of SRD5AIII amino acids may be fused with those of another protein such as keyhole limpet hemocyanin and antibody produced against the chimeric molecule.

The purified polypeptides of the invention can be used for diagnostic, therapeutic and screening purposes. This isozyme of 5α-reductase can be useful for developing novel approaches in preventing benign prostatic hyperplasia, preventing the development of prostate cancer and treating advanced prostate cancer, either to prolong the duration of remission after androgen deprivation therapy or to induce re-remission upon recurrence of prostate cancer after androgen deprivation therapy.

In one embodiment, this invention provides diagnostic methods using antibodies or polynucleotides described herein. These can be used to diagnose conditions which are characterized by aberrant expression of SRD5AIII. Such assays can also be used to monitor the effect of various therapeutic approaches. The antibodies can be prepared by methods described above. Diagnostic assays for SRD5AIII include methods which utilize the antibody and a label to detect SRD5AIII in human body fluids or extracts of cells or tissues. The antibodies may be used with or without modification, and may be labeled by joining them, either covalently or non-covalently, with a reporter molecule. Such reporter molecules are well known in the art. Methods for detecting levels of SRD5AIII protein include standard methods such as ELISA, RIA, and FACS. Normal or standard values for SRD5AIII expression can be established from normal subjects.

The polynucleotides which can be used for diagnostic purposes include oligonucleotide sequences, antisense RNA and DNA molecules. The polynucleotides may be used to detect and quantify SRD5AIII gene expression in biopsied tissues. The diagnostic assay may be used to distinguish between absence, presence, and excess expression of SRD5AIII, and to monitor regulation of SRD5AIII levels during therapeutic intervention. The polynucleotide sequences encoding SRD5AIII may be used in Southern or northern analysis, dot blot, or other membrane-based technologies; in PCR technologies; or chip assays utilizing fluids or tissues from patient biopsies to detect altered SRD5AIII expression. Such qualitative or quantitative methods are well known in the art.

In one embodiment, the level of expression of the SRD5AIII isozyme can be determined by detecting the polynucleotides or protein and further comparing the level of expression to that of the other 5α-reductase isozyme such as SRD5AI and SRD5AII. Suitable primers for detection of SRD5AIII are provided herein.

In one embodiment, hybridization with PCR probes which are capable of detecting polynucleotide sequences, including genomic sequences, encoding SRD5AIII may be used to identify nucleic acid sequences which encode SRD5AIII. Those skilled in the art will recognize that the specificity of the probe and the stringency of the hybridization or amplification (maximal, high, intermediate, or low) will determine whether the probe identifies only naturally occurring sequences encoding SRD5AIII, alleles, or related sequences.

The SRD5AIII protein can also be used in screening assays for the identification of substances that may inhibit or otherwise modify or alter the enzymatic function of the isozyme. The use of recombinantly-produced SRD5AIII for this purpose is of particular benefit because the naturally occurring SRD5AIII is present in only small quantities and often difficult to purify. The screening assays of the invention, in preferred embodiments, can employ the SRD5AIII directly from the recombinant host in which it is produced. This can be achieved by simply expressing the selected SRD5AIII within the recombinant host (such as a eukaryotic host), followed by preparing a crude homogenate which includes SRD5AIII. The homogenate may be purified (such as on an affinity column). A portion of the crude or purified homogenate is then mixed with an appropriate substrate of the SRD5AIII, e.g., T along with the candidate substance to be tested. By comparing the action of the SRD5AIII on the selected substrate in the presence or absence of the candidate substance, one can obtain information regarding the ability of the candidate substance to affect the activity of the SRD5AIII. Further, the ability of this isozyme can also be compared to SRD5AI and SRD5AII isozymes.

In these assays, generally the reaction mixture containing the SRD5AIII, substrate and candidate substance is allowed to incubate for a selected amount of time, and the resultant incubated mixture subjected to a separation means in order to separate the substrate remaining in the reaction mixture from any product produced. Then, the amount of each is measured versus a control to which no candidate substance has been added. This measurement can be made at various time points where velocity data is desired. From this, one may determine the ability of the candidate substance to alter or modify the function of the enzyme.

Methods for the separation of the substrate from product are well known in the art. For example, thin layer chromatographic methods (TLC), as TLC-based methods are quick, accurate, inexpensive and quite sensitive. Other useful techniques include HPLC and spectrophotometric and gas chromatographic/mass spectrophotometry. Those skilled in the art may recognize that any technique may be employed which is capable of differentiating between the enzyme substrate and product, and can be used to determine enzymatic function such as by identifying or quantifying the substrate and product.

Identified inhibitory agents can be used alone or in combination with SRD5AI and/or SRD5AII inhibitors to effect complete blockade of the 5α-reducing capability of prostatic tissue thereby reducing DHT to levels insufficient for activation of the androgen receptor. This could prove a much more effective treatment for benign prostatic hyperplasia as well as prove useful for the treatment of advanced prostate cancer. Male pattern baldness and adolescent acne may also respond to complete 5α-reductase inhibition.

The results described in the examples presented below provide data to indicate successful expression of this protein, generation of specific antibodies and determination of expression in CaP. These examples are intended to be illustrative and should not be construed as restrictive in any way.

EXAMPLE 1

This example describes the expression of SRD5AIII protein. cDNA cloned into the *E. coli* expression vector, pME18S-FL3 was obtained from Dr. Juergen Reichert of the University of Southern California Medical Center. This group was unable to express the protein. Our experiments with this vector also failed. The pMEI 8S-FL3 promoter is SR alpha, which contains SV-40 and part of the LTR of human leukemia virus type 1. We identified a point mutation, c→a, at promoter base 240 and insertion of an adenine after promoter base 363. The mutated vector was replaced by pET100/D TOPO that successfully expressed SRD5AIII protein in *E. coli*. The protein was toxic in *E. coli*, which may be due to inclusion body formation and membrane destabilization.

EXAMPLE 2

This example demonstrates the differential expression of SRD5AI and SRD5AII in benign and recurrent prostate tumors. Our data (Titus et al. Clin Cancer Res 2005; 11(12): 4365-4371) suggests that the 5α-reducing capability of recurrent CaP shifts from SRD5AII toward SRD5AI. Nuclear immunostaining (Table 1) exhibited higher SRD5AI than SRD5AII expression in recurrent CaP (12.5:1) compared to AS-benign prostate (5:1) and AS-CaP (3:1). Tissue miocroarray immunohistochemistry and color video image analysis were performed as X described previously (Titus et al. Clin Cancer Res 2005; 11(12):4365-4371). The tissue miocroarray sections were visually scored blinded to patient androgen status. Epithelial cell SRD5AI and II nuclear and cytoplasmic immunostaining were semiquantitatively assessed using a scale ranging from 0 (no expression) to 3 (strong expression) in each of 100 nuclei or cells yielding a visual score ranging from 0 to 300 (Miyamoto et al. J Urol 1993; 149:1015-9).

Shown in Table 1 are nuclear visual scores of steroid SRD5AI and SRD5AII immunostaining in tissue microarray of androgen-stimulated benign prostate (AS-BP), androgen-stimulated prostate cancer (AS-CaP) and recurrent CaP.

TABLE 1

| Nuclear |      | AS-BP | AS-CaP | Recurrent CaP |
|---------|------|-------|--------|---------------|
| SRD5AI  | Mean | 150   | 115    | 125           |
|         | SD   | 55    | 71     | 57            |
| SRD5AII | Mean | 29    | 37     | 10            |
|         | SD   | 20    | 27     | 10            |

Figure 1A:
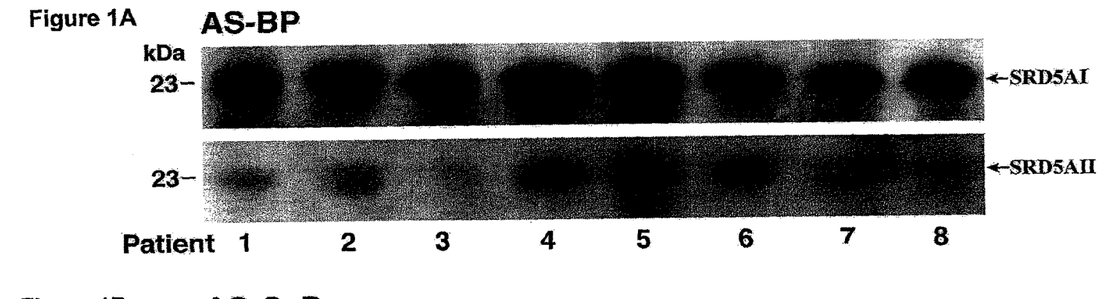
FIGS. 1A-1C are photographic representations of immunoblot analysis of SRD5AI and SRD5AII in human prostate tissues. Immunoblotting was performed using purified SRD5AI and SRD5AII polyclonal antibodies and lysates from (1A) androgen-stimulated benign prostate, (1B) androgen-stimulated CaP and (1C) recurrent CaP specimens. Molecular weight standard proteins are indicated in kilodaltons (kDa).
Figure 1B:
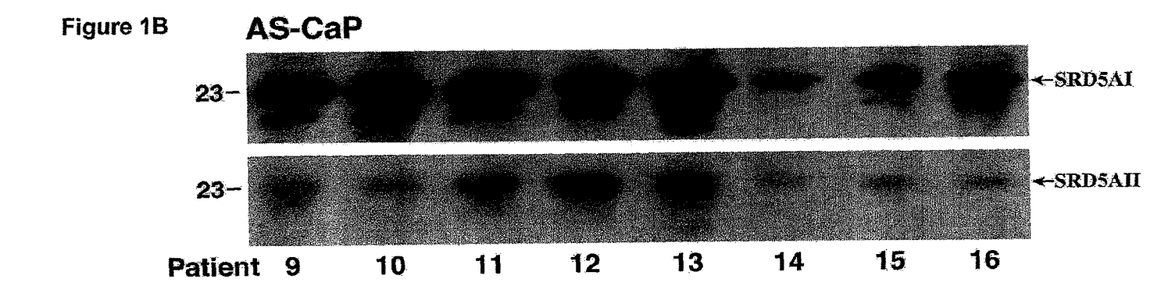
Figure 1C:
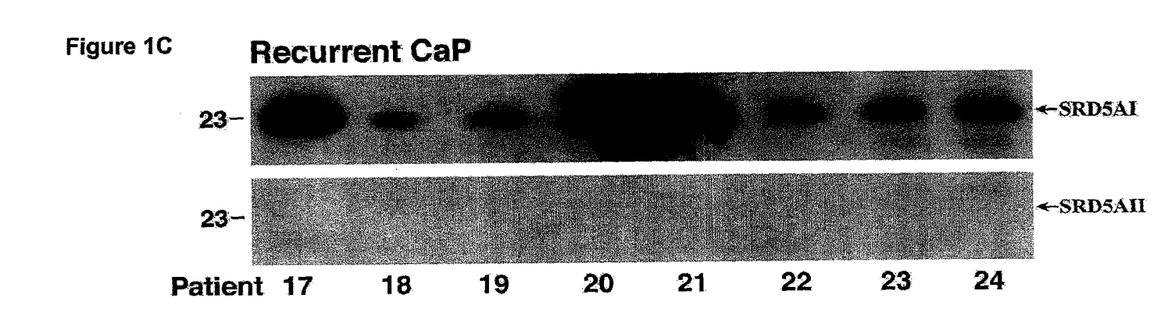

Immunoblots confirmed immunohistochemistry; SRD5AI was expressed in recurrent CaP specimens and SRD5AII was not detected (FIG. 1).

The activity of SRD5AI determined as described in Example 5 and as previously described (Titus et al. Clin Cancer Res 2005; 11:4365-4371; Pratis et al. J Steroid Biochem Mol Biol 2000; 75:75-82; Lowry et al. J Biol Chem 1951; 193:265-75; Godin et al. Steroids 1999; 64:767-769). The activity of SRD5AI (114.4 pmoles/mg epithelial protein/min) was 3.7-fold higher thanSRD5AII (30.7 pmoles/mg epithelial protein/min) in recurrent CaP (Table 2).

As shown in Table 2, the median and range of steroid SRD5A activity at acidic and neutral pH (pmoles/mg epithelial tissue/min) demonstrates 5α-reductase reducing capability shifts to isozyme I in recurrent CaP. The isozyme results in clinical specimens (Table 2) demonstrate greater SRD5AI than SRD5AII activity in recurrent CaP.

TABLE 2

| Specimen      | SRD5AII pH 5.5    | SRD5AI pH 7.5       | n  |
|---------------|-------------------|---------------------|----|
| AS-BP         | 319.7 (45.6-486.7)| 166.9 (103.3-335.1) | 12 |
| AS-CaP        | 86.2 (0-117.9)    | 75.6 (15.7-83.2)    | 12 |
| Recurrent CaP | 30.7 (0-60.4)     | 114.4 (12.2-214.9)  | 12 |

EXAMPLE 3

We have designed sequence-specific primers for determination of levels of mRNA for SRD5AIII. Total RNA was extracted from human cancer specimens using RNeasy Mini Kit (Qiagen). The 400 ng of total RNA from each sample was reverse-transcribed into cDNA using random primers and Superscript™ II reverse transcriptase (Invitrogen). The RT reaction was performed at 25° C. for 10 min, 48° C. for 30 min and 95° C. for 5 min. Pre-made primers and probes for the SRD5AI and SRD5AII target genes were purchased from ABI. The sequence of primer set and probe for SRD5AII are: forward, 5'-ATTTGTGTACTCACTGCTCAATCGA-3' (SEQ ID NO:3); reverse, 5'AGGCAGTGCCTCT-GAGAATGA-3' (SEQ ID NO:4); probe, 5'FAM-AGGCCT-TATCCAGCTAT-3'MGB (SEQ ID NO:5); "FAM" is 6-Carboxyfluorescein; "MGB" is minor groove binder, a non-fluorescence probe. The primers and probe for SRD5AIII are provided in Example 5. PCR reactions were performed using the 7300 real-time PCR system from Applied Biosystems (ABI) with a total volume of 25 ul reaction mixture containing 8 ng cDNA, 1× TaqMan Universal PCR Master Mix (ABI) and 1× primers and probe mix. The PCR conditions used for all reactions were: 95° C. for 10 min, 40 amplification cycles at 95° C. for 15 sec (denaturing), and 60° C. for 1 min (annealing and extension). The amounts of SRD5AI, SRD5AII, and SRD5AIII in prostate cancer tissues were normalized to an endogenous housekeeping gene, beta-glucuronidase, and $2^{-\Delta\Delta C_T}$ ("comparative $C_T$ quantitative real-time PCR") was used to calculate expression levels relative to AS-benign prostate tissue. Prostate cancer specimens from 7 men were analyzed for SRD5AI, SRD5AII and a potential isozyme SRD5AIII mRNA levels in CaP cell lines and clinical specimens using qRT-PCR. The mRNA levels in 3 AS-CaP and 3 recurrent CaP specimens were normalized to a single AS-BP specimen. Gene expression levels obtained from CaP specimens are shown in Table 3, which summarizes the quantitative analysis of SDR5A isozyme mRNA levels using qRT-PCR in androgen-stimulated prostate cancer (AS-CaP) and recurrent CaP (RCaP) relative to androgen-stimulated benign prostate (AS-BP). Mean SRD5AI mRNA levels decreased 30% in AS-CaP and 75% in recurrent CaP specimens relative to AS-BP. SRD5AII gene expression was negligible in AS-CaP and not detected in recurrent CaP. SRD5AIII mRNA levels decreased 30% in AS-CaP and 45% in recurrent CaP relative to AS-BP. Results obtained from mean mRNA levels in 3 AS-CaP specimens suggest a gene expression gradient of SDR5AI≧SDR5AIII>>SDR5AII. The 3 recurrent CaP specimens mean mRNA levels suggest an expression gradient of SDR5AIII>SDR5AI>>SDR5AII. These results on the relative contribution of the 3 isozymes of 5α-reductase at the message level suggest that 1) mRNA for SDR5AI and SDR5AII correlate well with the SDR5A isozyme protein levels and enzymatic activities described above and 2) mRNA for SDR5AIII is expressed at similar levels in recurrent CaP and AS-CaP and maintained at higher levels than either SRD5AI or SRD5AII in recurrent CaP.

TABLE 3

| Specimen # | AS-CaP | RCaP |
|---|---|---|
| SRD5AI | | |
| 1 | 0.38 | 0.13 |
| 2 | 1.34 | 0.35 |
| 3 | 0.41 | 0.29 |
| Mean ± SD | 0.71 ± 0.55 | 0.26 ± 0.11 |
| SRD5AII | | |
| 1 | 0.07 | 0.00 |
| 2 | 0.06 | 0.01 |
| 3 | 0.01 | 0.00 |
| Mean ± SD | 0.047 ± 0.032 | 0.003 ± 0.006 |
| SRD5AIII | | |
| 1 | 0.76 | 0.73 |
| 2 | 1.01 | 0.48 |
| 3 | 0.29 | 0.47 |
| Mean ± SD | 0.69 ± 0.36 | 0.56 ± 0.15 |

EXAMPLE 4

This example describes the generation of monoclonal antibodies directed to SDR5AIII. Monoclonal antibodies directed against potential isozyme SRD5AIII were produced by immunizing mice with 3 synthetic amino-terminal peptides that are selected as candidate epitopes. BioSource, Inc. (Hopkinton, Mass.) synthesized MAPWAEAEHSALNPLR (SEQ ID NO:6) corresponding to amino acids 1-16, FQD-LIRYGKTKCGEPSR (SEQ ID NO:7) corresponding to amino acids 46-62 and DLIRYGKTKCGEPSRPAA (SEQ ID NO:8) corresponding to amino acids 48-65. Each peptide was coupled to keyhole limpet hemocyanin (peptide-KLH), for immunization, and to albumin (peptide-BSA), for detection. The peptides were coupled using the EDC (1-ethyl-3-(3-dimethylaminopropyl) carbodimide hydrochloride method (Pierce, Rockford, Ill.).

Three groups of 4 BALB/c mice (6-8 weeks old) were immunized 3 times with each of 3 peptide-KLH antigens and boosted 4 days before fusion. Mice were immunized using intraperitoneal injections on days 0, 14, 28 and 70. Mice were cared for according to institutional guidelines and the Institutional Animal Care and Use Committee (Protocol 996M) approved all experiments.

Splenocytes and the myeloma cells P3X63 Ag8U.1 (ATCC CRL 1597) were fused using a modified protocol (Mishell et al. W H Freeman and Company, New York 1980:486). Washed splenocytes and myeloma cells were mixed at 4:1 ratio and centrifuged. The cell pellet was resuspended in 1 ml of 35% polyethylene glycol (PEG 1450, ATCC) and 5% DMSO in DMEM medium. After one minute, the suspension was diluted in 9 ml prewarmed medium. The suspension was seeded in 96-well plates at 100 ul/well (2.5×10/well) in DMEM medium supplemented with 20% fetal bovine serum (HyClone, Logan, Utah), 100 uM HAT (hypoxanthine, aminopterin, thymidine fusion medium) and endothelial cell mitogen (ECM) (Biomedical Technologies, Stoughton, Mass.). On days 3 and 6, half of the spent medium was replaced by fresh HAT medium containing 1 ug/ml fresh ECM. Monoclonal antibody production in culture supernatants was assayed on day 11 using enzyme-linked immunosorbent assay (ELISA).

Immunoassay ELISA For detecting anti-peptide antibodies, indirect ELISA was performed as follows: Microtiter plates (MaxiSorp, Nalge Nunc, Rochester, N.Y.) were coated with 50 ul of 2 ug/ml PBS of peptide-BSA overnight at 4° C. 100 ul of blocking buffer (Milk Diluent/Blocking solution; KPL, Gaithersburg, Md.) was added to each well and incubated 60 min. After washing with PBS containing 0.05% Tween 20, 50 ul of hybridoma supernatants diluted in blocking buffer were added and incubated 1 hr at room temperature. After washing, the bound monoclonal antibodies were incubated with horseradish peroxidase (HRP)-labeled goat anti-mouse IgG (Jackson ImmunoResearch, Grove, Pa.) for 1 hr and detected using TMB Peroxidase Substrate (KPL).

Positive clones were transferred to 24-well plates. Culture supernatants were screened for reactivity to negative controls.

Figure 2:
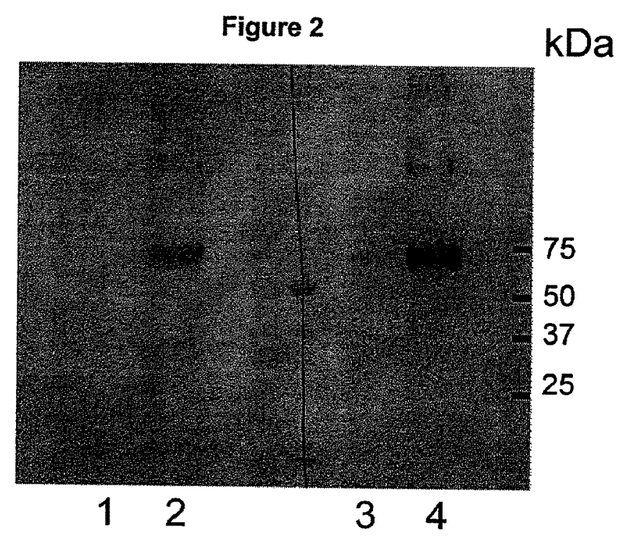
FIG. 2 is a photographic representation of an immunoblot analysis of a monoclonal antibody generated against a peptide of SEQ ID NO:7.

Among 8 monoclonal antibodies positive in the first screening, 3 were negative in the rescreening, probably due to the loss of antibody production, and one nonspecifically bound to ELISA plates. Two monoclonal antibodies reacted to peptide 1-16 AA using ELISA (Table 4) and Western Blot (FIG. 2). Two monoclonal antibodies against peptide 2 (peptide 48-65) were detected using ELISA (Table 5) but no band was found on Western blots (data not shown). The specific hybridomas were cloned using a limiting dilution method.

Western Blots Twenty ug of peptide/albumin conjugate were separated using SDS-Page on 10% gel. The transferred PVDF membrane was blocked using Milk Diluent/Blocking solution (KPL) and incubated with each hybridoma spent medium diluted 1:10. The bound monoclonal antibodies were detected with goat anti-mouse IgG-HRP (Jackson ImmunoResearch) and TMB Membrane Peroxidase Substrate (KPL).

TABLE 4

ELISA titer of mouse anti-peptide 1-16 in hybridoma supernatant

| Dilution | Absorbance 450 | |
|---|---|---|
| | Hybridoma 1 | Hybridoma 2 |
| 1:50 | 1.89 | 2.04 |
| 1:100 | 1.17 | 2.19 |
| 1:200 | 0.91 | 1.69 |
| 1:400 | 0.34 | 1.13 |
| 1:800 | — | 0.65 |
| 1:1600 | — | 0.21 |

TABLE 5

ELISA titer of mouse anti-peptide 48-65 in hybridoma supernatant

| Dilution | Absorbance 450 | |
|---|---|---|
| | Hybridoma 3 | Hybridoma 4 |
| 1:3 | 0.82 | 0.66 |
| 1:6 | 0.69 | 0.51 |
| 1:12 | 0.44 | 0.16 |
| 1:24 | 0.40 | — |

Aliquots (10 ug protein) of peptide-BSA complex were separated using SDS PAGE and transferred to PVDF membranes. Membranes were probed with hybridoma 1 supernatant (A) and hybridoma 2 supernatant (B). Western blotting showed that the mouse anti-peptide antibodies bound peptide conjugated to albumin (lanes 2 and 4) but didn't react with albumin (lanes 1 and 3). The molecular weight of approximately 70 kDa corresponded with the predicted molecular weight of 16 amino acids (2 kDa) and albumin (68 kDa).

EXAMPLE 5

Materials and Methods

Cell culture and reagents. CV-1 cells (monkey kidney; ATCC-CCL-70) and HEK 293 cells (human embryonic kidney, ATCC-CRL-1573™) were cultured in Dulbecco's modified Eagle medium (DMEM) with 10% fetal bovine serum (Mediatech Cellgro, Herndon, Calif.) at 37° C. and 5% $CO_2$. Anti-6X-His, anti-X-press, and Positope were purchased from Invitrogen (Carlsbad, Calif.), peroxidase-conjugated affinipure goat anti-mouse IgG were purchased from Jackson ImmunoResearch (West Grove, Pa.) and an enzymatic protein deglycosylation kit was purchased from Sigma (St. Louis, Mo.).

Plasmid construction. A 1183-bp fragment encodes a fusion protein in which the polyhistidine (6X-His) and X-press epitopes are attached to the N-terminal end of presumed SRD5AIII. This construct was excised from the PET100/D-SRD5AIII expression vector by digesting with BglII and SacI endonucleases. The resulting fragment was cloned into pDC316 (Microbix, Toronto, Ontario), using BglII and SacI to generate an adenovirus shuttle plasmid.

Generation and amplification of recombinant adenovirus. pDC316-SRD5AIII shuttle plasmid containing the murine CMV promoter was cotransfected with pBHG loxp (Microbix), that contains the adenovirus type 5 genome with E1 and E3 region deletions, into HEK 293 cells using SuperFect® transfection system (Qiagen, Valencia, Calif.) according to the manufacturer's protocol. HEK 293 cells and medium were harvested when cytopathic effects appeared. Cells were subjected to three cycles freeze/thaw lysis in a dry ice-ethanol bath and centrifuged at 5000 rpm for 5 min at 4° C. to remove cellular debris. The supernatant was saved as virus stock. Adenovirus (Ad-SRD5AIII) was propagated by infecting HEK 293 cells with virus stock in tissue culture medium without serum for three hr and overlayed with DMEM/10% FBS medium. Infected cells were collected when viral cytopathic effects were identified and processed as described. The Ad-SRD5AIII titer will be determined at a later time.

CV-1 cell Ad-SRD5AIII infection and immunoblot analysis. CV-1 cells (70-80% confluent in 6-well plates) were transiently infected with Ad-SRD5AIII that express the 6X-His and X-press-tagged SRD5AIII in serum free DMEM medium for three hr and grown in DMEM with 10% FBS at 37° C. and 5% $CO_2$ for 21 hr. The cells were harvested for immunoblot analysis and RNA extraction. Cell lysates were resolved on 10% SDS-PAGE gel. Immunoblots using anti-6X-His and anti-X-press antibodies were performed using standard procedures and the SRD5AIII fusion protein was detected using electrochemical luminescence (Pierce, Rockford, Ill.) according to the manufacturer's protocol.

SRD5AIII polymerase chain reaction (PCR). Total RNA was isolated from infected and uninfected CV-1 cells using RNeasy Mini Kit (Qiagen). RNA samples (3 µg) were reverse-transcribed using reverse transcriptase (Invitrogen). cDNA was amplified by PCR using SRD5AIII gene specific primers; forward, 5'-CGG AAC AAG GGT TCC TGC TGA CCC TAC TGC T-3' (SEQ ID NO:9); reverse, 5'-TGA GTC AAG GGA GCT TTC CTA TGC TTC GGG TA-3' (SEQ ID NO:10). PCR amplification was performed at 95° C. for 2 min; and 30 cycles of 95° C. for 30 sec, 51° C. for 30 sec, and 72° C. for 1 min; and 72° C. for 10 min. The PCR product was resolved on 1% agarose gel containing 0.2 µg/ml ethidium bromide in TAE buffer, and the band of interest was visualized under UV light.

Solubilization and deglycosylation of CV-1-expressed SRD5AIII. In an attempt to increase the solubility or mobility of expressed SRD5AIII protein on SDS-PAGE, cell extracts of Ad-SRD5AIII infected CV-1 cells were treated with inclusion body solubilization reagent (Pierce) or deglycosylation enzymes (Sigma), respectively, according to the manufacturer's instructions.

Recombinant SRD5AIII in vitro assays. Ad-SRD5AIII infected CV-1 cells and uninfected CV-1 control cells were prepared and assayed for SRD5AIII using methods of Titus et al. (Titus et al. Clin Cancer Res 2005; 11:4365-4371) and Pratis et al. (Pratis et al. J Steroid Biochem Mol Biol 2000; 75:75-82). All steps prior to incubation were carried out at 4° C. SRD5AIII specific activity was expressed in pmol/mg protein/hr using Ad-SRD5AIII infected CV-1 cells.

Ad-SRD5AIII infected CV-1 cells or uninfected CV-1 cells were homogenized in 0.5 ml ice-cold homogenization buffer (50 mM potassium phosphate [pH 7.4], 0.25M sucrose, 1 mM EDTA, 1 mM dithiothreitol, 1 mM fresh phenylmethylsulfonyl chloride, 1× Complete™ protease inhibitor [Roche, Indianapolis, Ind.] using a PowerGen 125 (Fischer Scientific) for two 10-second bursts and sonicated (Branson Sonifier CD200, SmilthKine) at 20% power for 15 one-second bursts. Final homogenates were centrifuged at 500×g for 1 min to remove particulate. The resulting cell free supernatants were placed on ice and used immediately. Protein concentrations were measured using the procedure of Lowry et al. (Lowry et al. J Biol Chem 1951; 193:265-75).

The buffer for all incubations contained 100 mM Tris-citrate, 0.5 mM dithiothreitol, 0.5 mM NADPH and 1 μCi $^3$H-testosterone (New England Nuclear, Boston, Mass.). Unlabeled testosterone (T) was added to final incubation concentration of 1 μM. Incubations were performed in total volume 250 μl at pH 7.0 and pH 5.0. Enzymatic reaction began when 50 μl cell homogenate (350 μg protein) was mixed gently for 5 sec and incubated for 1 hr in a 37° C. shaking water bath. The incubations were quenched with 1 ml ice-cold chloroform/methanol (8:2, vol/vol), vortexed vigorously and placed on ice after centrifugation. The organic phase was separated from the aqueous phase, transferred to a new test tube, and dried. Uninfected CV-1 homogenate was added to control incubations. All incubations were performed in duplicate under protein and time linearity.

The conversion of T to dihydrotestosterone (DHT), androstanedione and androsterone was analyzed using thin layer chromatography (TLC, 33). Isolated tritiated steroids were dissolved in 40 μl chloroform/acetone (9:1) containing internal standards (0.2 mg/ml T, DHT, androstenendione and androstanedione, Sigma-Aldrich, St. Louis, Mo.), and separated using silica-coated plates and chloroform/acetone (9:1) mobile phase. The developed plates were visualized using iodine vapor. The chromatographic zones corresponding to reference steroids were scraped into vials containing 500 μl ethanol and vortexed. Liquid scintillation cocktail (8 ml Ecoscint, National Diagnostics, Atlanta, Ga.) was added. The samples were assayed for tritium using a liquid scintillation counter (Packard TC 2100TR). Control incubations were analyzed as described above.

The amount of radioactive DHT, androstanedione and androsterone was calculated as percent total radioactivity ($^3$H) recovered from the thin layer chromatography lane. Uninfected CV-1 homogenate and blank values were subtracted to calculate Ad-SRD5AIII CV1 metabolic rate.

Results

Figure 3:
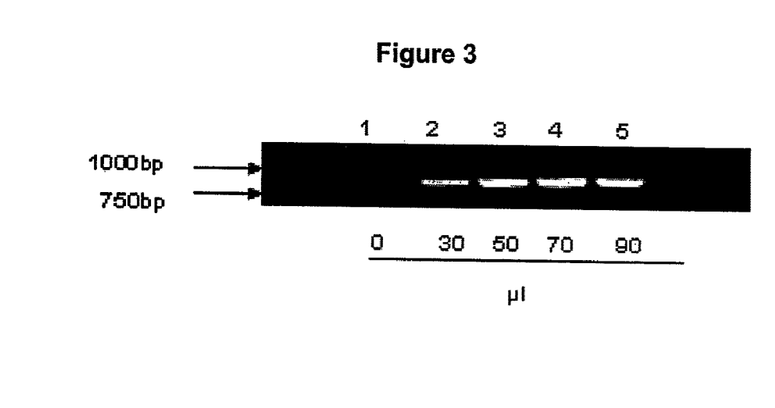
FIG. 3 is a photographic representation of an electrophoretic analysis of RTPCR products showing increased SRD5AIII mRNA expression levels in Ad-SRD5AIII infected CV-1 cells (lane 2-5) compared to control uninfected cells (lane 1). SRD5AIII mRNA expression levels increased in proportional to the amount of Ad-SRD5AIII virus stock supernatant administered that increased from 30 μl to 70 μl across lanes 2-5.

SRD5AIII transcription in Ad-SRD5AIII infected CV-1 cells. Gene specific RT-PCR primers were used to amplify SRD5AIII to determine whether SRD5AIII was transcribed in adenovirus infected CV-1 cells. SRD5AIII mRNA levels increased in a dose-dependent manner (FIG. 3).

Figure 4A:
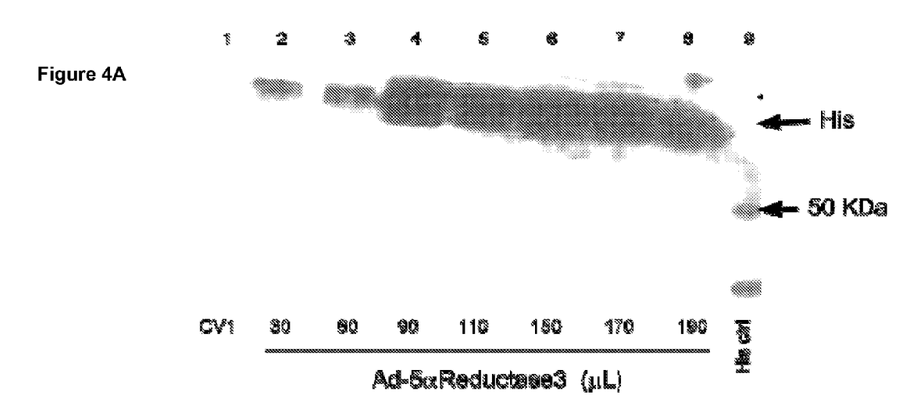
FIGS. 4A-4C are photographic representations of immunoblot analysis of Ad-SRD5AIII protein expression in CV-1 cells using anti-6X-His or anti-X-press antibodies. Anti-6X-His antibody (4A) was used to analyze cell lysates from uninfected CV-1 cells (lane 1) and CV-1 cells infected with increasing volumes of Ad-SRD5AIII virus stock (lanes 2-8) to detect SRD5AIII protein expression. A 50 kDa polypeptide, Positope, recognized by both anti-6X-His and anti-X-press antibodies was used as a positive control (lane 9). CV-1 cells were infected for 3, 6 or 24 hr and SRD5AIII protein expression detected using anti-6X-His (4B) and anti-X-press (4C) antibodies.
Figures 4B, 4C:
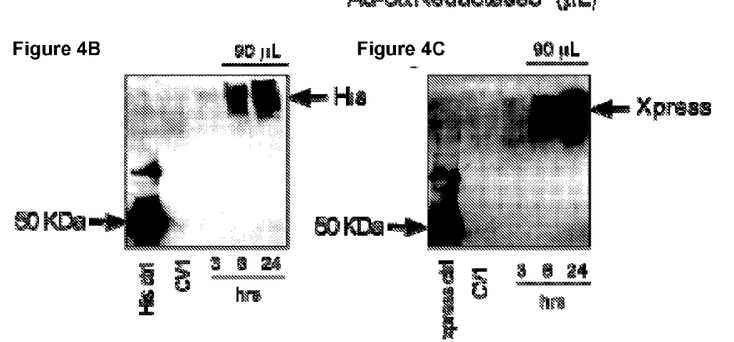
Figure 5A:
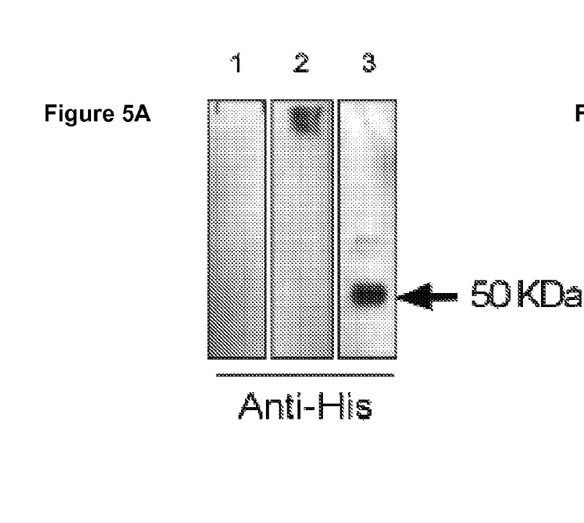
FIGS. 5A and 5B are photographic representations of immunoblot analysis from Ad-SRD5AIII infected CV-1 cell lysates. (5A) Immunoblot analysis using anti-6X-His antibody of uninfected CV-1 cells (lane 1), infected CV-1 cells (lane 2, 90 μl virus stock) and 6X-His/X-press Positope fusion protein control (lane 3). (5B) Immunoblot analysis of cell lysates treated with inclusion body solubilization reagent and dialyzed to refold proteins. Anti-6X-His or anti-X-press antibodies were used to detect SRD5AIII in infected CV-1 cells (lane 1, 90 μl virus stock), uninfected CV-1 cells (lane 2) and 6X-His/X-press Positope fusion protein control (lane 3).
Figure 5B:
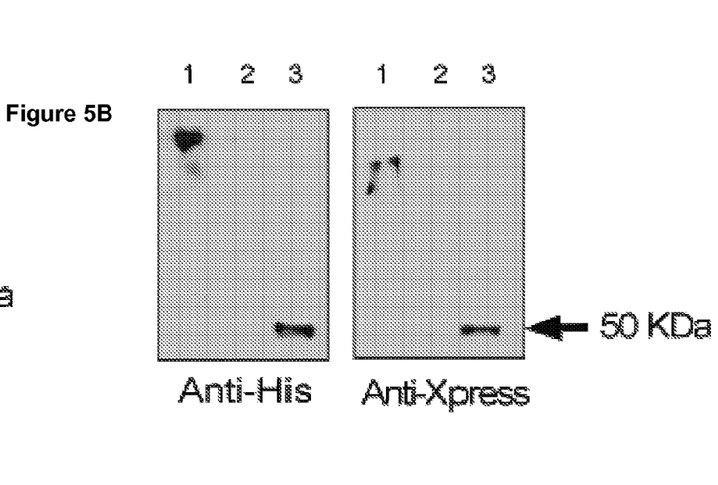
Figure 6A:
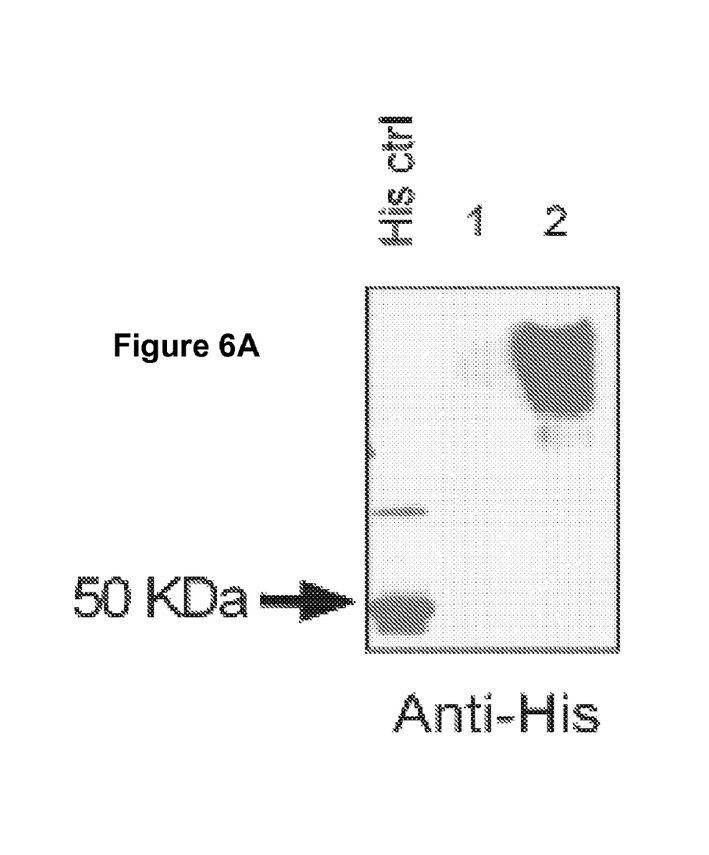
FIGS. 6A and 6B are photographic representations of immunoblots analysis of Ad-SRD5AIII infected CV-1 cell lysates deglycosylated and probed using anti-6X-His (6A) and anti-X-press (6B). Immunoblot lanes are 6X-His/X-press Positope fusion protein control, uninfected CV1 cells (lane 1) and infected CV1 cells (lane 2, 90 μl virus stock).
Figure 6B:
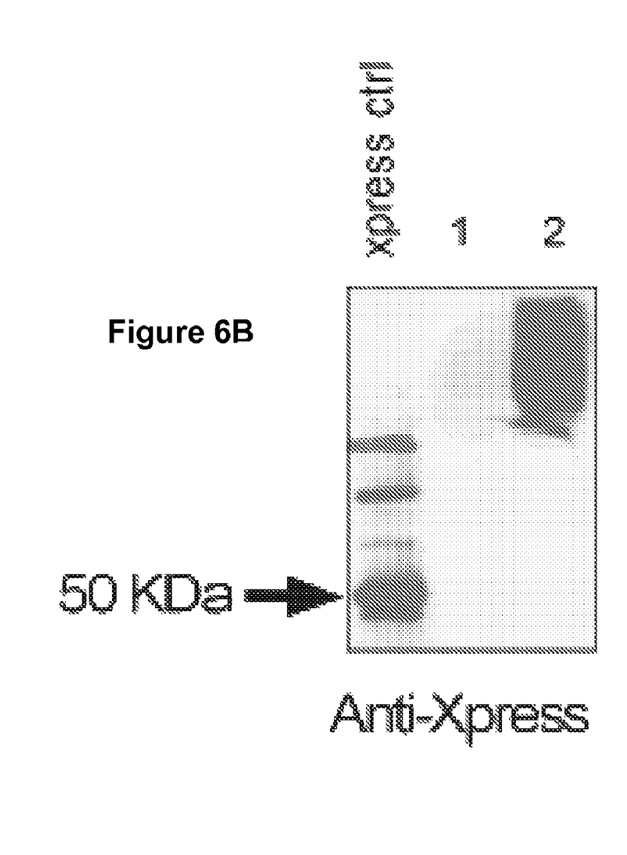
Figure 7:
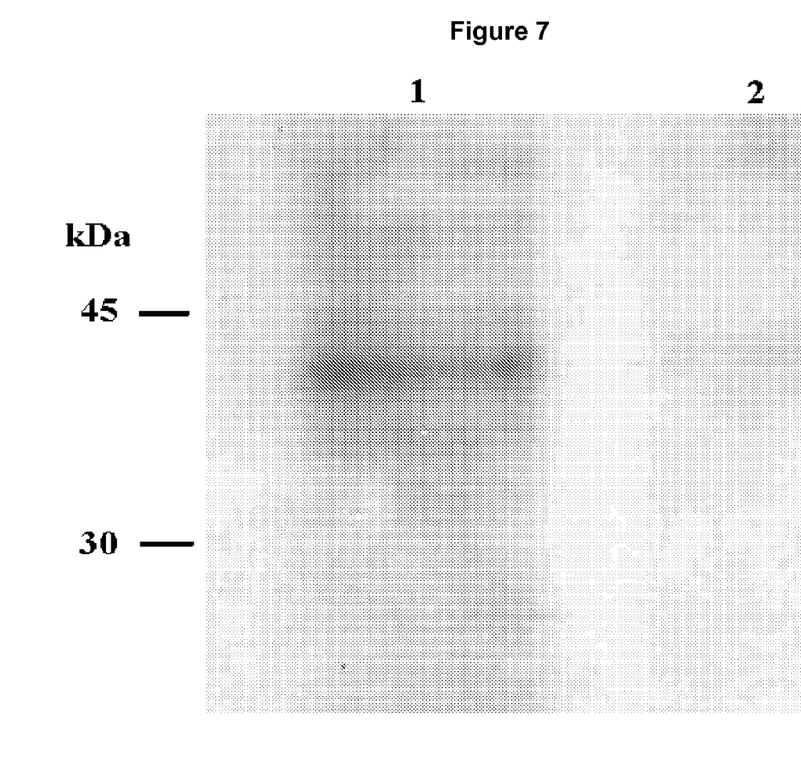
FIG. 7 is a photographic representation of immunoblot analysis of Ad-SRD5AIII infected CV-1 cell lysates, 50 μg (lane 1) and 25 μg of protein (lane 2) probed using anti-X-press antibody.

Anti-6X-His and anti-X-press antibodies were used to evaluate the expression level of 6X-His and X-press-tagged SRD5AIII in infected CV1 cells. Immunoblot analysis of cell lysates using anti-6X-His and anti-X-press revealed that SRD5AIII expression increased in cells infected with Ad-SRD5AIII (FIG. 4). However, the molecular weight of the detected band was higher than the expected SRD5AIII molecular weight of about 37 kDa. This result raised the possibility that aggregation and/or glycosylation might reduce mobility of SRD5AIII protein. Cell lysates treated with inclusion bodies solubilization reagent demonstrated no change in the mobility of the putative SRD5AIII band on SDS-PAGE (FIG. 5A). The same result was obtained after dialyzing the solubilization reagent-treated cell lysates (FIG. 5B). Cell extracts deglycosylated using an enzymatic protein deglycosylation kit before immunoblot analysis revealed no change in the mobility of the putative SRD5AIII. Whether the polysaccharide was removed from the protein has not been confirmed using purified His-tagged recombinant protein and mass spectrometry to prove SRD5AIII sequence or posttranslational modification (FIG. 6). However, Ad-SRD5AIII CV-1 cell lysate preparation and sonication resulted in visualization of an approximately 37 kDa protein on immunoblot probed with anti-X-press antibody (FIG. 7). The sonication may have released SRD5AIII protein from the inclusion body allowing a small amount of protein to migrate to appropriate molecular weight. The androgen 5α-reducing activity of recombinant SRD5AIII isozyme was determined at pH 5.0 (n=1) and pH 7.0 (n=3) using standard, previously described techniques (see, Titus et al. Clin Cancer Res 2005; 11:4365-4371; Pratis et al. J Steroid Biochem Mol Biol 2000; 75:75-82; Lowry et al. J Biol Chem 1951; 193:265-75; Godin et al. Steroids 1999; 64:767-769). SRD5AIII enzyme activity was not detected at pH 5.0 using 1 μM T substrate. The conversion of T to DHT and androstanedione was detected at pH 7.0 incubations using 5 μM T substrate. The pH optimum for SRD5AIII appears to be pH 7.0. The specific activity calculated after subtracting background activity was 15.6 pmol/mg protein/hour. This indicates that SRD5AIII isozyme may have a similar pH profile as the SRD5AI isozyme.

The foregoing description of the specific embodiments is for the purpose of illustration and is not to be construed as restrictive. From the teachings of the present invention, those skilled in the art will recognize that various modifications and changes may be made without departing from the spirit of the invention.

The invention claimed is:

1. A method of detecting recurrent prostate cancer in an individual comprising the steps of:
   a) obtaining a biopsy sample of prostate from the individual;
   b) determining the level of expression of SRD5AIII gene or protein;
   c) comparing the level of expression of SRD5AIII to expression of SRD5AI and SRD5AII,
   wherein an increased expression of SRD5AIII relative to the expression of SRD5AI and SRD5AII is indicative of recurrent prostate cancer.

2. The method of claim 1, wherein in step b) the level of SRD5AIII mRNA is determined.

3. The method of claim 2, wherein the level of mRNA is determined by reverse transcriptase polymerase chain reaction (RTPCR).

4. The method of claim 3, wherein the RTPCR is performed using a first primer having the sequence of SEQ ID NO:9 and a second primer having the sequence of SEQ ID NO:10.

5. The method of claim 1, wherein in step b) the level of SRD5AIII protein is determined.

* * * * *

SEQUENCE LISTING

```
<160> NUMBER OF SEQ ID NOS: 10

<210> SEQ ID NO 1
<211> LENGTH: 1294
<212> TYPE: DNA
<213> ORGANISM: human
<220> FEATURE:
<223> OTHER INFORMATION:

<400> SEQUENCE: 1
ctgagaccgg tgcgccgcgc gctagtggcc gctcttccgc gggctagcgg gcggtggggg        60
cgccagcagc gcggaaggcg ggcacgcggg ccatggctcc ctgggcggag gccgagcact       120
```

-continued

```
cggcgctgaa cccgctgcgc gcggtgtggc tcacgctgac cgccgccttc ctgctgaccc      180
tactgctgca gctcctgccg cccggcctgc tcccgggctg cgcgatcttc caggacctga      240
tccgctatgg gaaaaccaag tgtgggagc cgtcgcgccc cgccgcctgc cgagcctttg       300
atgtccccaa gagatatttt tcccactttt atatcatctc agtgctgtgg aatggcttcc      360
tgctttggtg ccttactcaa tctctgttcc tgggagcacc ttttccaagc tggcttcatg      420
gtttgctcag aattctcggg gcggcacagt tccagggagg ggagctggca ctgtctgcat      480
tcttagtgct agtatttctg tggctgcaca gcttacgaag actcttcgag tgcctctacg      540
tcagtgtctt ctccaatgtc atgattcacg tcgtgcagta ctgttttgga cttgtctatt      600
atgtccttgt tggcctaact gtgctgagcc aagtgccaat ggatggcagg aatgcctaca      660
taacagggaa aaatctattg atgcaagcac ggtggttcca tattcttggg atgatgatgt      720
tcatctggtc atctgcccat cagtataagt gccatgttat tctcggcaat ctcaggaaaa      780
ataaagcagg agtggtcatt cactgtaacc acaggatccc atttggagac tggtttgaat      840
atgtttcttc ccctaactac ttagcagagc tgatgatcta cgtttccatg gccgtcacct      900
ttggggttcca caacttaact tggtggctag tggtgacaaa tgtcttcttt aatcaggccc      960
tgtctgcctt tctcagccac caattctaca aagcaaatt tgtctcttac ccgaagcata      1020
ggaaagcttt cctaccatttt tgttttaag ttaacctcag tcatgaagaa tgcaaaccag      1080
gtgatggttt caatgcctaa ggacagtgaa gtctggagcc aaagtacag tttcagcaaa       1140
gctgtttgaa actctccatt ccatttctat accccacaag ttttcactga atgagcatgg      1200
cagtgccact caagaaaatg aatctccaaa gtatcttcaa agaataaata ctaatggcag      1260
aaaaaaaaaa aaaaaaaaaa aaaaaaaaaa aaaa                                  1294
```

<210> SEQ ID NO 2
<211> LENGTH: 318
<212> TYPE: PRT
<213> ORGANISM: human
<220> FEATURE:
<223> OTHER INFORMATION:

<400> SEQUENCE: 2

```
Met Ala Pro Trp Ala Glu Ala Glu His Ser Ala Leu Asn Pro Leu
                5                  10                  15

Arg Ala Val Trp Leu Thr Leu Thr Ala Ala Phe Leu Leu Thr Leu
                20                  25                  30

Leu Leu Gln Leu Leu Pro Pro Gly Leu Leu Pro Gly Cys Ala Ile
                35                  40                  45

Phe Gln Asp Leu Ile Arg Tyr Gly Lys Thr Lys Cys Gly Glu Pro
                50                  55                  60

Ser Arg Pro Ala Ala Cys Arg Ala Phe Asp Val Pro Lys Arg Tyr
                65                  70                  75

Phe Ser His Phe Tyr Ile Ile Ser Val Leu Trp Asn Gly Phe Leu
                80                  85                  90

Leu Trp Cys Leu Thr Gln Ser Leu Phe Leu Gly Ala Pro Phe Pro
                95                  100                 105

Ser Trp Leu His Gly Leu Leu Arg Ile Leu Gly Ala Ala Gln Phe
                110                 115                 120

Gln Gly Gly Glu Leu Ala Leu Ser Ala Phe Leu Val Leu Val Phe
                125                 130                 135

Leu Trp Leu His Ser Leu Arg Arg Leu Phe Glu Cys Leu Tyr Val
                140                 145                 150
```

```
Ser Val Phe Ser Asn Val Met Ile His Val Val Gln Tyr Cys Phe
            155                 160                 165

Gly Leu Val Tyr Tyr Val Leu Val Gly Leu Thr Val Leu Ser Gln
            170                 175                 180

Val Pro Met Asp Gly Arg Asn Ala Tyr Ile Thr Gly Lys Asn Leu
            185                 190                 195

Leu Met Gln Ala Arg Trp Phe His Ile Leu Gly Met Met Met Phe
            200                 205                 210

Ile Trp Ser Ser Ala His Gln Tyr Lys Cys His Val Ile Leu Gly
            215                 220                 225

Asn Leu Arg Lys Asn Lys Ala Gly Val Val Ile His Cys Asn His
            230                 235                 240

Arg Ile Pro Phe Gly Asp Trp Phe Glu Tyr Val Ser Ser Pro Asn
            245                 250                 255

Tyr Leu Ala Glu Leu Met Ile Tyr Val Ser Met Ala Val Thr Phe
            260                 265                 270

Gly Phe His Asn Leu Thr Trp Trp Leu Val Val Thr Asn Val Phe
            275                 280                 285

Phe Asn Gln Ala Leu Ser Ala Phe Leu Ser His Gln Phe Tyr Lys
            290                 295                 300

Ser Lys Phe Val Ser Tyr Pro Lys His Arg Lys Ala Phe Leu Pro
            305                 310                 315

Phe Leu Phe

<210> SEQ ID NO 3
<211> LENGTH: 25
<212> TYPE: DNA
<213> ORGANISM: artificial sequence
<220> FEATURE:
<221> NAME/KEY:
<222> LOCATION:
<223> OTHER INFORMATION: forward SRD5AII primer

<400> SEQUENCE: 3
atttgtgtac tcactgctca atcga                                         25

<210> SEQ ID NO 4
<211> LENGTH: 21
<212> TYPE: DNA
<213> ORGANISM: artificial sequence
<220> FEATURE:
<221> NAME/KEY:
<222> LOCATION:
<223> OTHER INFORMATION: reverse SRD5AII primer

<400> SEQUENCE: 4
aggcagtgcc tctgagaatg a                                             21

<210> SEQ ID NO 5
<211> LENGTH: 17
<212> TYPE: DNA
<213> ORGANISM: artificial sequence
<220> FEATURE:
<221> NAME/KEY:
<222> LOCATION:
<223> OTHER INFORMATION: SRD5AII probe

<400> SEQUENCE: 5
aggccttatc cagctat                                                  17

<210> SEQ ID NO 6
```

```
<211> LENGTH: 16
<212> TYPE: PRT
<213> ORGANISM: artificial sequence
<220> FEATURE:
<221> NAME/KEY:
<222> LOCATION:
<223> OTHER INFORMATION: SRD5AIII derived peptide

<400> SEQUENCE: 6

Met Ala Pro Trp Ala Glu Ala Glu His Ser Ala Leu Asn Pro Leu
                 5                  10                  15
Arg

<210> SEQ ID NO 7
<211> LENGTH: 17
<212> TYPE: PRT
<213> ORGANISM: artificial sequence
<220> FEATURE:
<221> NAME/KEY:
<222> LOCATION:
<223> OTHER INFORMATION: SRD5AIII derived peptide

<400> SEQUENCE: 7

Phe Gln Asp Leu Ile Arg Tyr Gly Lys Thr Lys Cys Gly Glu Pro
                 5                  10                  15
Ser Arg

<210> SEQ ID NO 8
<211> LENGTH: 18
<212> TYPE: PRT
<213> ORGANISM: artificial sequence
<220> FEATURE:
<221> NAME/KEY:
<222> LOCATION:
<223> OTHER INFORMATION: SRD5AIII derived peptide

<400> SEQUENCE: 8

Asp Leu Ile Arg Tyr Gly Lys Thr Lys Cys Gly Glu Pro Ser Arg
                 5                  10                  15
Pro Ala Ala

<210> SEQ ID NO 9
<211> LENGTH: 31
<212> TYPE: DNA
<213> ORGANISM: artificial sequence
<220> FEATURE:
<221> NAME/KEY:
<222> LOCATION:
<223> OTHER INFORMATION: forward SRD5AIII primer

<400> SEQUENCE: 9
cggaacaagg gttcctgctg accctactgc t                              31

<210> SEQ ID NO 10
<211> LENGTH: 32
<212> TYPE: DNA
<213> ORGANISM: artificial sequence
<220> FEATURE:
<221> NAME/KEY:
<222> LOCATION:
<223> OTHER INFORMATION: reverse SRD5AIII primer

<400> SEQUENCE: 10
tgagtcaagg gagctttcct atgcttcggg ta                             32
```